US009877649B2

(12) United States Patent
Tamkin et al.

(10) Patent No.: US 9,877,649 B2
(45) Date of Patent: Jan. 30, 2018

(54) PHOTOREFRACTION METHOD AND PRODUCT

(71) Applicant: Gobiquity, Inc., Scottsdale, AZ (US)

(72) Inventors: John Michael Tamkin, Pasadena, CA (US); Peter-Patrick de Guzman, Los Angeles, CA (US)

(73) Assignee: Gobiquity, Inc., Scottsdale, AZ (US)

( * ) Notice: Subject to any disclaimer, the term of this patent is extended or adjusted under 35 U.S.C. 154(b) by 0 days.

(21) Appl. No.: 15/333,078

(22) Filed: Oct. 24, 2016

(65) Prior Publication Data

US 2017/0112378 A1   Apr. 27, 2017

Related U.S. Application Data

(60) Provisional application No. 62/245,811, filed on Oct. 23, 2015.

(51) Int. Cl.
*A61B 3/00* (2006.01)
*A61B 3/10* (2006.01)
(Continued)

(52) U.S. Cl.
CPC ........... *A61B 3/154* (2013.01); *A61B 3/0025* (2013.01); *A61B 3/0041* (2013.01); *A61B 3/103* (2013.01);
(Continued)

(58) Field of Classification Search
USPC ................................................. 351/200–246
See application file for complete search history.

(56) References Cited

U.S. PATENT DOCUMENTS

| 2010/0097573 A1* | 4/2010 | Verdooner ............... A61B 3/14 351/206 |
| 2013/0235346 A1* | 9/2013 | Huang .................... A61B 3/152 351/208 |

(Continued)

FOREIGN PATENT DOCUMENTS

| JP | 2011-200281 A | 10/2011 |
| KR | 10-2014-0079864 A | 6/2014 |

(Continued)

*Primary Examiner* — Mohammed Hasan
(74) *Attorney, Agent, or Firm* — George C. Rondeau, Jr.; Davis Wright Tremaine LLP

(57) ABSTRACT

Systems and methods are provided for performing a photorefractive assessment. The system comprises a computing device including an image-capturing device, a display device, and a computer application that is executable on the computing device and operable to perform a method including receiving input specifying subject information, capturing an image using the image-capturing device containing eye pupils of a subject, and analyzing the image captured to determine a distance between the subject and the image-capturing device using the subject information and predetermined interpupillary distance information. A remediation action may be performed if the distance determined is not within an appropriate distance range for the photorefractive assessment. An illuminance level of the environment may be analyzed using the image captured to determine whether lighting conditions are appropriate for performing the photorefractive assessment. Various aspects of the image captured may be analyzed to determine whether to perform a remediation action.

21 Claims, 10 Drawing Sheets

(51) Int. Cl.
  *A61B 3/15*  (2006.01)
  *A61B 3/103* (2006.01)
  *A61B 3/11*  (2006.01)
  *A61B 5/00*  (2006.01)

(52) U.S. Cl.
  CPC .............. *A61B 3/111* (2013.01); *A61B 3/152* (2013.01); *A61B 5/6898* (2013.01); *A61B 2560/0431* (2013.01)

(56) References Cited

U.S. PATENT DOCUMENTS

2014/0268060 A1   9/2014  Lee et al.
2016/0073870 A1*  3/2016  Bailey ................... A61B 3/085
                                                351/202

FOREIGN PATENT DOCUMENTS

KR    10-2014-0103900 A   8/2014
WO       2014-195623 A1  12/2014

* cited by examiner

PHOTOREFRACTION METHOD AND PRODUCT

CROSS-REFERENCE TO RELATED APPLICATIONS

This application claims priority to U.S. Provisional Application No. 62/245,811, filed Oct. 23, 2015, entitled "PHOTOREFRACTION METHOD AND PRODUCT;" which is hereby incorporated by reference in its entirety.

FIELD OF INVENTION

The present invention is directed to systems and methods for performing a photorefractive assessment.

BACKGROUND

Photorefraction is a method for assessing the refractive error in a patient's vision, and is based upon a reflection of a flash source 10 from the retina 12. In FIG. 1, the light 15 from the flash source 10 propagates to the retina 12. In an eye that can accommodate or focus on the flash source 10, reflected light bundle 14 from the retina returns to the flash source 10 and does not enter the camera pupil 16 adjacent to the flash source 10. An image 18 of the eyes captured by the camera pupil 16 will appear dark or have a red eye pupil 20. A red eye pupil 20 is due to diffuse reflection (scattered light) of the flash source 10 within the eye of light-pigment retinas, so that the scattered light picks up the hue of blood vessels within the eye. Dark-pigmented retinas absorb the flash, and thus a dark eye pupil is imaged by the camera. If the eye cannot focus on a flash image plane 11 of the flash source 10 commonly due to a refractive error, then the specular reflected light 22 will be spread out, and some of the specular reflected light 22 will be collected by the camera pupil 16, as shown in FIG. 3. The specular reflected light 22 in an image 24 captured by the camera pupil 16 appears to form a yellow crescent 26 in the eye pupil 20, as shown in FIG. 4. The width of the crescent 26 is proportional to the residual refractive error of the patient's eye, which is not able to focus on the camera pupil 16. The width of the crescent 26 depends upon the 1) distance between the camera pupil 16 and the patient, 2) the separation of the flash source 10 to the camera pupil 16, 3) the diameter of patient's pupil 20, and 4) the patient's accommodative refractive error.

DETAILED DESCRIPTION

Figure 1:
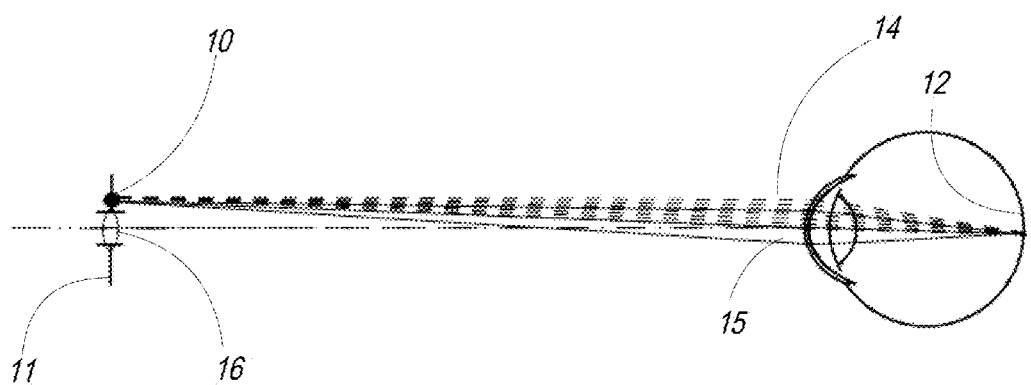
FIG. 1 illustrates light emitted from a flash source and reflected from a retina of a focused eye as focused light.
Figure 2:
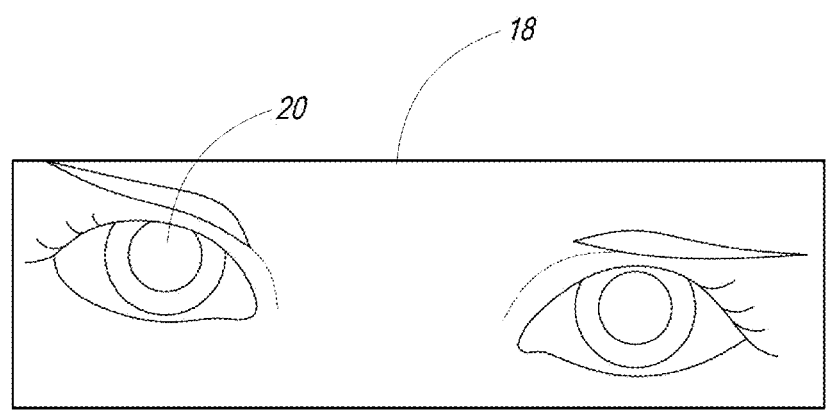
FIG. 2 illustrates an image captured of the reflected light of FIG. 1.
Figure 3:
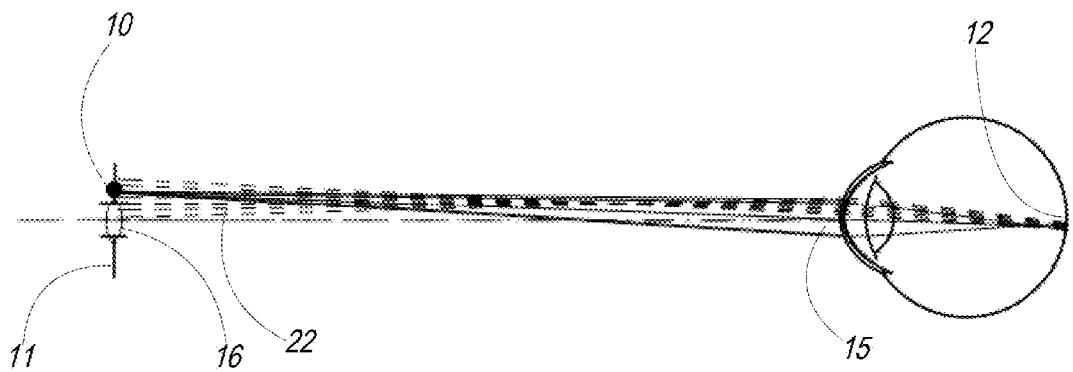
FIG. 3 illustrates light emitted from a flash source and reflected from a retina of an unfocused eye as unfocused light.
Figure 4:
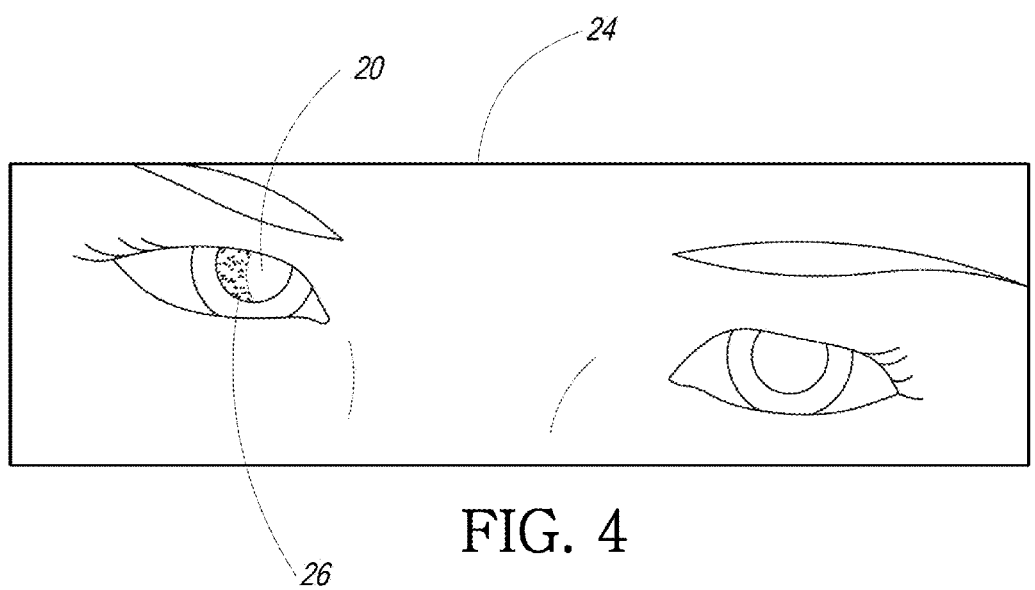
FIG. 4 illustrates an image captured of the reflected light of FIG. 3.
Figure 5A:
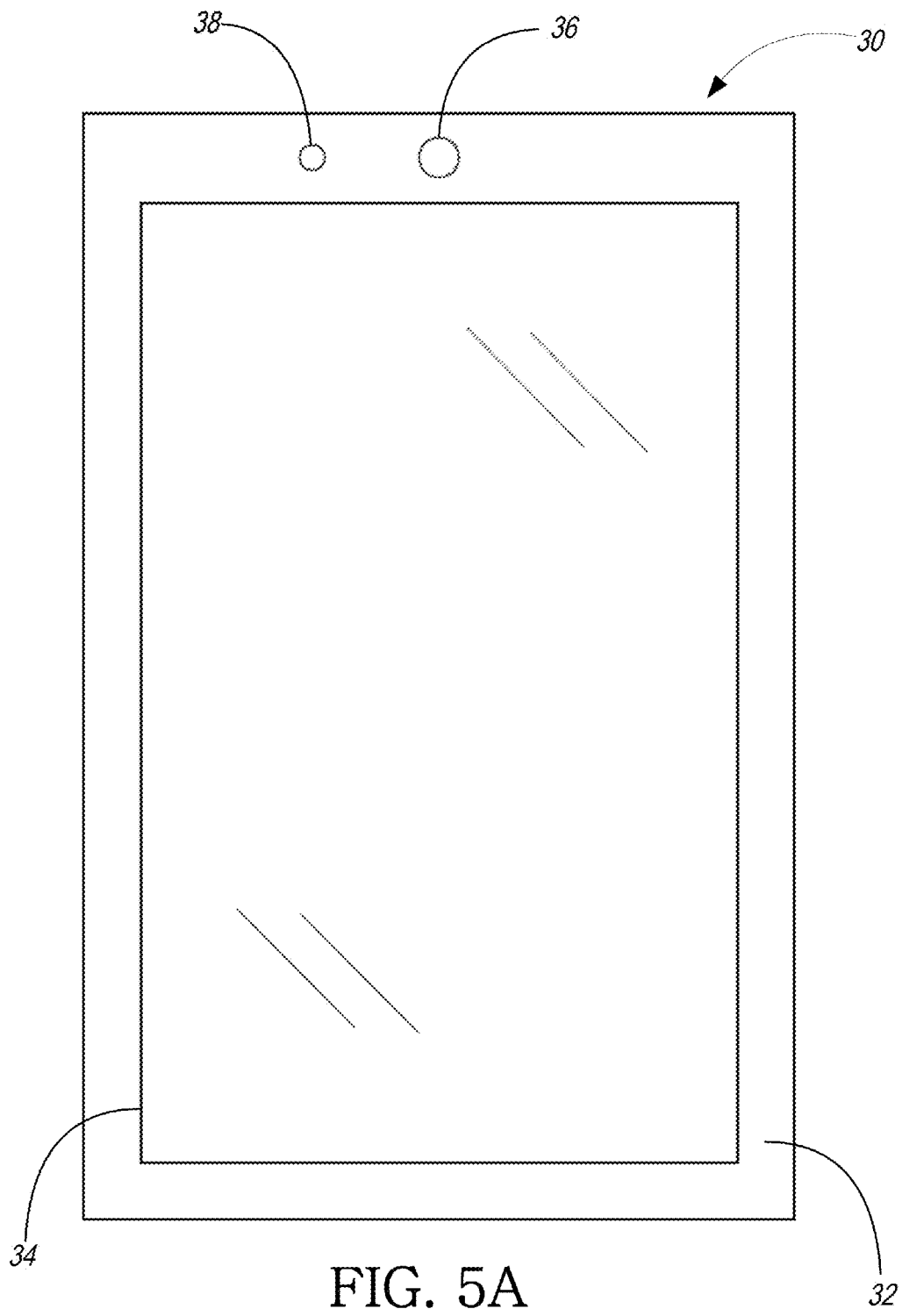
FIG. 5A illustrates a front view of a computing device in accordance with an embodiment of the present invention.

Systems and methods for performing photorefraction assessments are provided according to the present disclosure. FIG. 5A illustrates a computing device 30 that may be used to provide the functionality described herein. The computing device 30 is operated by user, such as a physician, another health care provider, parent, or the like. The computing device 30 may include a conventional operating system configured to execute software applications and/or programs. By way of non-limiting examples, computing device 30 may be a personal computer (e.g., a laptop), a smart phone, or tablet computer. Generally, the computing device 30 may include devices that are readily commercially available (e.g., smart phones, tablet computers, etc.), and or may include devices specifically configured for this particular application.

Figure 5B:
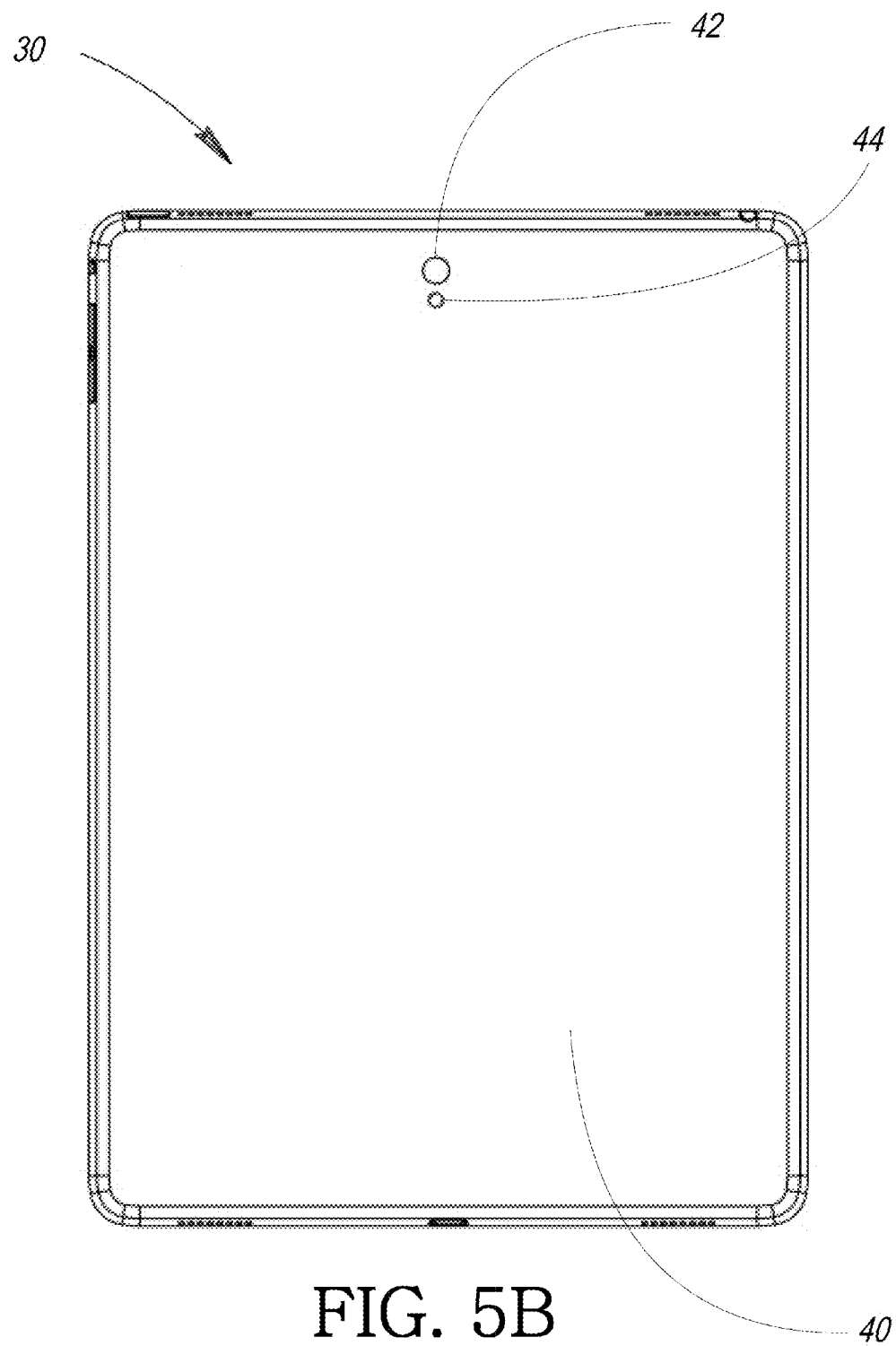
FIG. 5B illustrates a rear view of the computing device of FIG. 5A.

The computing device 30 has a front side 32 provided with a display device 34 for real-time display, and may include an image-capturing device 36 (i.e., a camera), and a light-generating device 38 (e.g., flash, LED light), as shown in FIG. 5A. The display device 34 may be touch-sensitive (e.g., touchscreen) and operable to control the aspects of the computing device 30, such as the operating system, applications, and hardware (e.g., image-capturing device, light-generating device). A back side 40 of the computing device 30 includes a light-generating device 42 (e.g., flash, LED light) and an image-capturing device 44 (i.e., a camera), as shown in FIG. 5B. The computing device 30 may be an iPad or iPhone produced by Apple®, or an Android® device, by way of non-limiting example. A computer application or software may be provided on the computing device 30 to use the image-capturing devices and/or the light-generating devices to capture images of a subject's eyes. In some instances, the light-generating devices 38 and 42 are respectively spaced apart at a distance from the camera pupil of the image-capturing devices 36 and 44. The distance spacing the light-generating device 42 apart from the image-capturing device 44 may be between 5 mm and 16 mm, for example.

Figure 6:
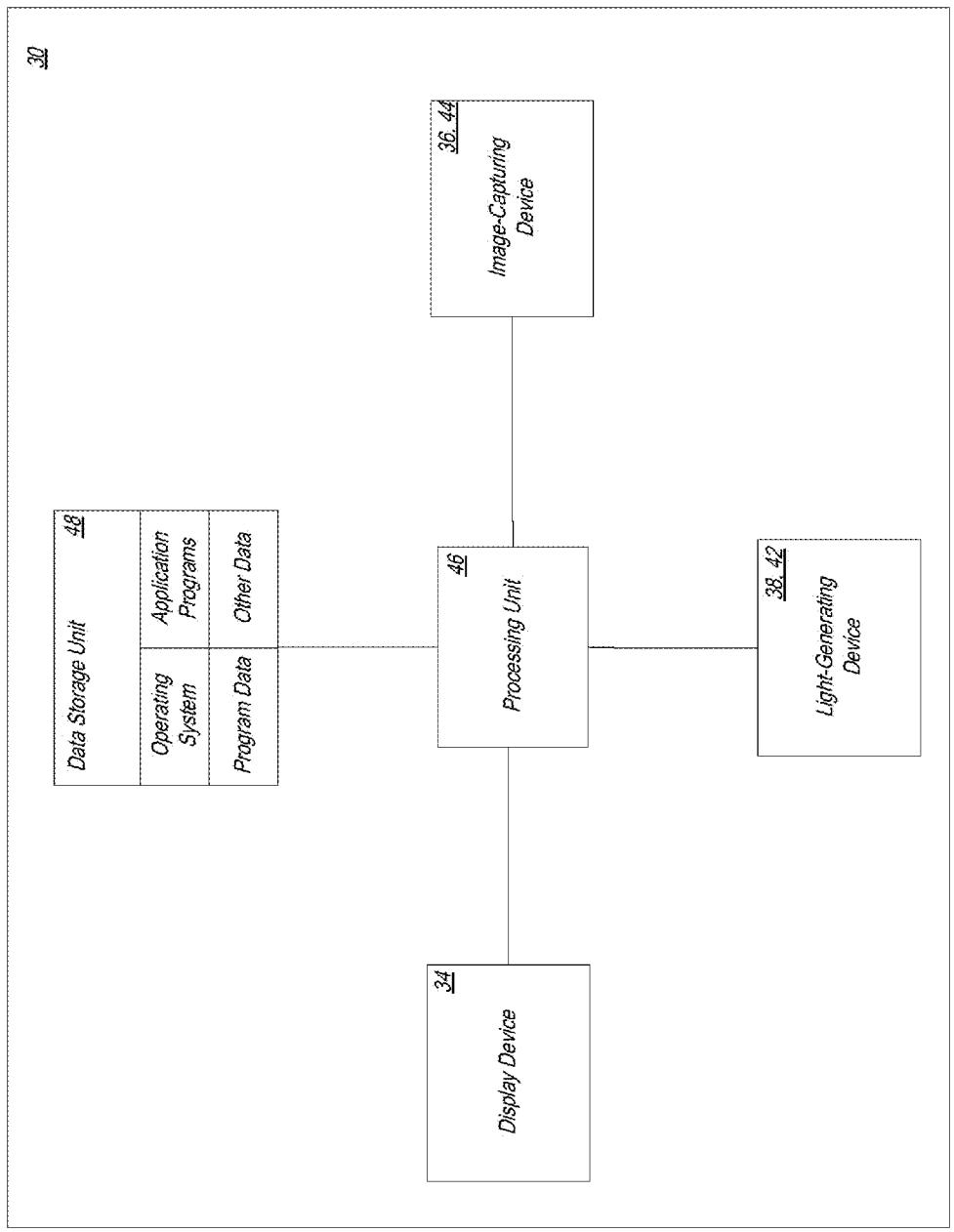
FIG. 6 illustrates a schematic view of the computing device of FIG. 5A.

The computing device 30 includes a processing unit 46 electronically coupled to several components, including a data storage unit 48, the display device 34, the light-generating devices 38 and 42, and the image-capturing devices 36 and 44, as shown in FIG. 6. The processing unit 46 may communicate with and/or control the components by sending and receiving electronic signals, including data and control signals. The data storage unit 48 is a non-transitory storage medium, such as hard drive for reading and writing data thereon, and may include one or more types of memory types (e.g., RAM, ROM, cache) known in the art. The data storage unit 48 may store different types of data, such as an operating system, one or more application programs, program data, and other data (e.g., word documents, media files, etc.). The data storage unit 48 has executable instructions that, as a result of execution on the processing unit 46, cause the processing unit to communicate with and control the components of the computing device 30.

The processing unit 46 electronically communicates with and controls the other components according to programming data on the data storage unit 48. For example, the processing unit 46 communicates with the display device 34 to display images thereon, and receives data from the touch screen of the display device for interacting with the computing device 30. The processing unit 46 sends independent control signals to the image-capturing devices 36 and 44 controlling the settings thereof and causing each of them to capture image data for transmission back to the processing unit 46. The processing unit 46 sends control signals independently to each of the light-generating devices 38 and 42 for generating light according to the control signal (e.g., at a specific timing, at a specific brightness, etc.).

The embodiments of the present systems and methods herein enable a user to perform a photorefraction assessment using an application provided on the computing device 30. The computing device 30 has an appropriate separation between the light-generating devices and the image-capturing device on each respective side (i.e., the front side 32 and the back side 40), providing a physical and computational platform adapted for calculating and estimating the subject's refractive error. An accurate refractive estimate requires controlled subject-to-camera distance, and a reasonable quality image. For example, the eyelids must not be shut, or occlude the eye pupil, and the subject must be looking at the camera. The computing power available on currently available computing devices is sufficient to support the methods disclosed herein to generate and provide real-time user feedback prior to capturing an image.

To administer the photorefractive assessment, the image-capturing device 36 or 44 must be facing the subject and spaced apart from the subject at a correct distance. It is possible to achieve the correct distance by using an assistive tool such as a string between subject and camera operator, or a stick of a certain length. While effective, these tools may be ergonomically clumsy, especially when evaluating the photorefraction of a young child or infant.

Figure 7:
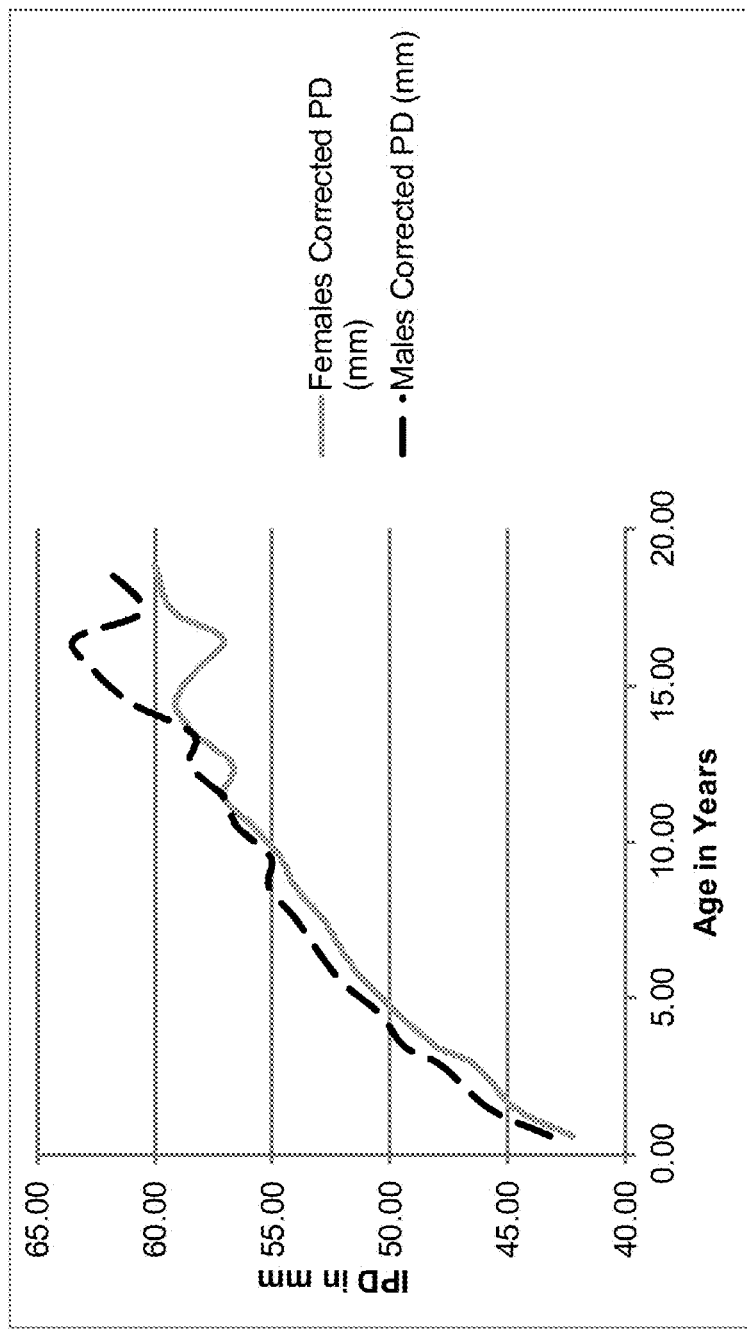
FIG. 7 illustrates a graph of interpupilary distance characterized as a function of age and sex.
Figure 8:
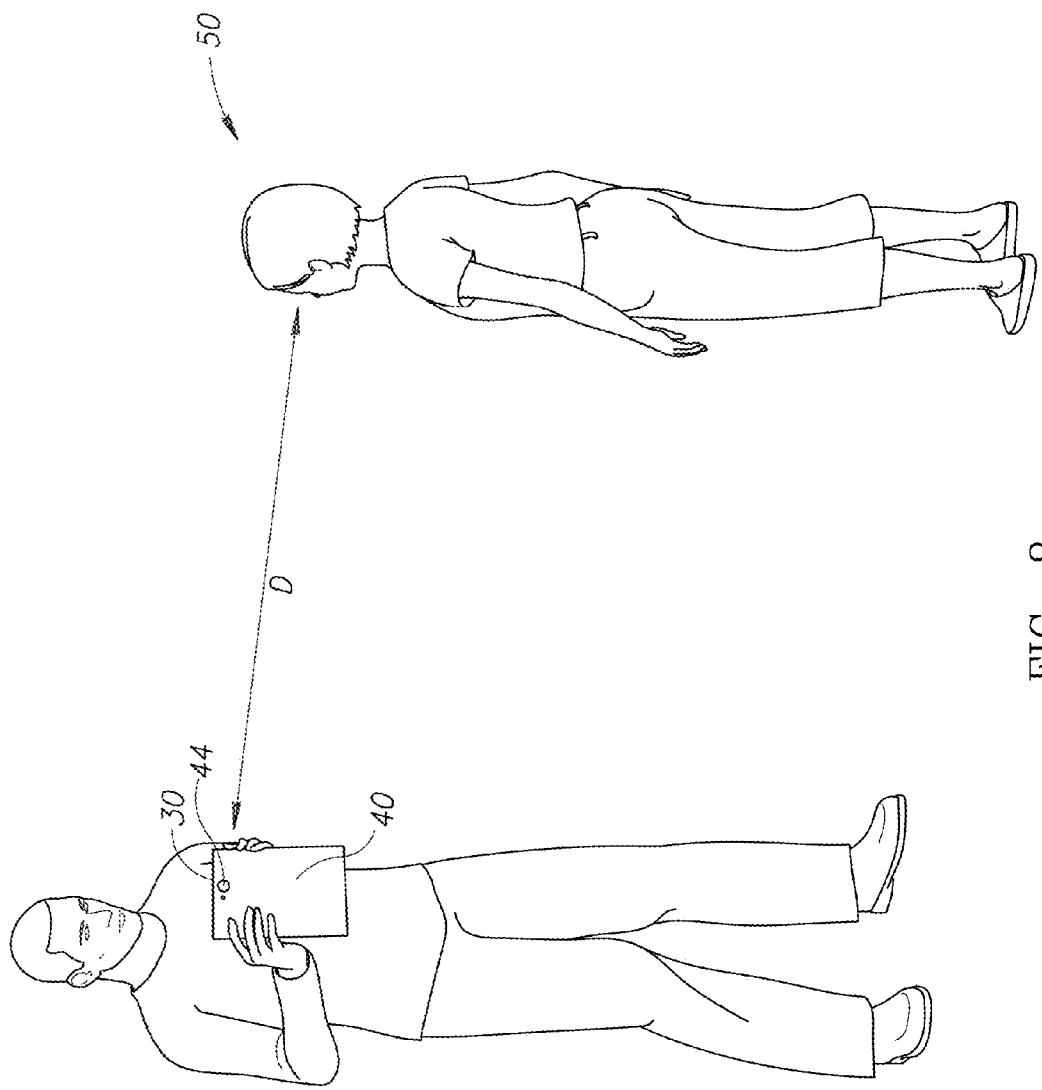
FIG. 8 illustrates the positioning of an operator in a subject during the visual acuity assessment.

The distance between a person's pupils, or interpupilary distance (IPD), is well-characterized as a function of age and sex, as shown in FIG. 7. The age-distance relationship is usable, in conjunction with other aspects of the method described below, to determine the distance D between a subject 50 and the image-capturing device 44 shown in FIG. 8. When the face of the subject 50 is imaged by the image-capturing device 44, the distance D of the camera relative to the face affects the degree of separation between the eyes of the subject 50. The computing device 30 is configured to indicate whether the image-capturing device 44 is positioned at an appropriate distance D to the subject 50, or whether the distance D is too close or too far from the subject 50. Therefore, cumbersome auxiliary tools are unnecessary in the present method.

Figure 9A:
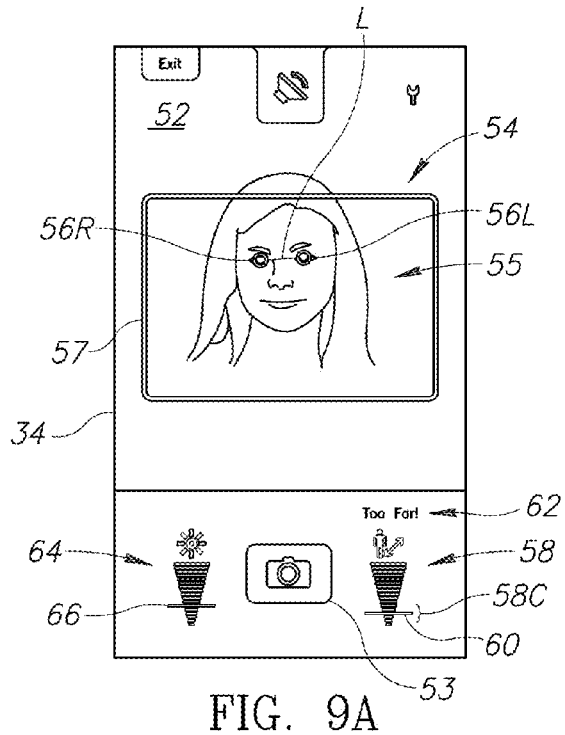
FIG. 9A illustrates a first screen of an application for administering a photorefractive assessment on a display device of the computing device of FIG. 5A.
Figure 9B:
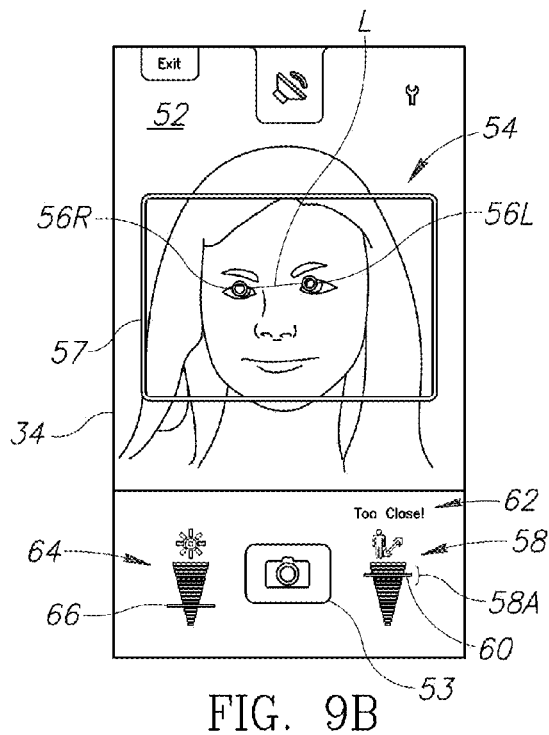
FIG. 9B illustrates a second screen of the application of FIG. 9A.
Figure 9C:
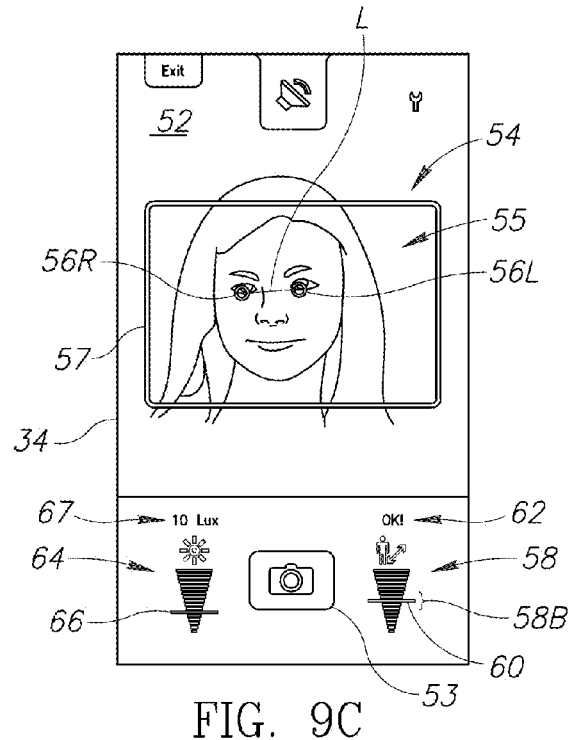
FIG. 9C illustrates a third screen of the application of FIG. 9A.

Embodiments of the systems and methods include a software program or application 52 (see FIGS. 9A-11) executing on the computing device 30. A user may store the application 52 on the data storage unit 48 and activate the application 52 via the display device 34. The application 52 is configured to analyze an image 54 of the subject and determine the distance D by measuring the interpupilary distance between the subject's left eye and right eye in the image 54, as shown in FIGS. 9A through 9C. The application 52 includes programming instructions that cause the processing unit 46 to interact with and control the image-capturing devices 36 and 44 to capture and display the image 54 of the subject 50 on the display device 34. The application 52 may include an image capture tool 53 causing the image-capturing device 44 to capture and store an image in the data storage unit 48. The digitized image 54 captured is constructed of pixels.

The application 52 comprises a facial recognition component configured to recognize a face 55 of the subject 50 in the image 54, and a distance-measuring component configured to determine a distance D between the subject 50 and the image-capturing device 44. The application 52 is configured to locate a left eye pupil 56L and a right eye pupil 56R of the face 55 of the subject 50 identified in the image 54 captured. The application 52 may include a frame 57 to assist the user to position the face 55 within a desired area of the display device 34. The application 52 generates position information corresponding to the pixel coordinates of the left eye pupil 56L and the right eye pupil 56R of the subject 50 in the image 54 captured. Given the pixel coordinates, the application 52 performs additional computation calculations and converts the separation of the eye pupils to a calculated distance value having a dimension comparable to the data tabulated for age stratified interpupilary distance. The calculated distance value is defined as a measured interpupilary distance (mIPD) in the current disclosure. The application 52 may generate a centerline L between the left eye pupil 56L and right eye pupil 56R corresponding to the mIPD. The application 52 may measure the length of the centerline L to determine the mIPD. The application 52 compares the mIPD and the IPD (corresponding to the patients age and sex), thereby determining the distance D. The application 52 determines whether the distance D determined is appropriate for performing a photorefractive assessment, and provides the user with an indication of whether to move the computing device 30 closer to or farther away from the subject 50. The centerline L may be displayed on the screen 34 or may be invisible to the user and maintained by the application 52 for analysis purposes.

The application 52 includes a distance indicator 58 that indicates whether the subject 50 is spaced apart at an appropriate distance D from the image-capturing device 44 (see FIGS. 9A through 9C). The distance indicator 58 includes a subject distance indicator 60 indicating the distance of the subject 50 to the image-capturing device 44. The distance indicator 58 may have different areas corresponding to distance ranges of the subject 50 from the image-capturing device 44. If the subject distance indicator 60 is positioned in a first area 58A of the distance indicator 58 (see FIG. 9B), the application 52 has determined that the face 55 of the subject 50 is too close to the image-capturing device 44. If the subject distance indicator 60 is positioned in a second area 58B of the distance indicator 58 (see FIG. 9C), the application 52 has determined that the face 55 of the subject is at an appropriate distance for capturing and storing an image using the image-capturing device 44 on which to perform photorefractive analysis. If the subject distance indicator 60 is located in a third area 58C of the distance indicator 58 (see FIG. 9A), the application 52 has determined that the face 55 of the subject 50 is too far from the image-capturing device 44. The first area 58A, the second area 58B, and the third area 58C may be differently colored regions, such as red, green, and red, respectively.

If the application 52 determines that the face 55 of the subject 50 is too close or too far from the image-capturing device 44, the application may perform a remediation action to help ensure that the image captured is satisfactory or optimal for performing photorefractive analysis. The remediation action may include displaying a distance status 62, indicating a status of the distance of the face 55 from the image-capturing device 44, such as "too far", "too close", or "OK!". Alternatively, the remediation action may disable the image-capturing tool 53 such that a user is unable to capture an image using the image-capturing device 44 unless the face 55 is at an appropriate distance D therefrom.

Other ancillary tools including artificial features such as a sticker with a predetermined size or diameter can be used to determine distance as well. The application 52 similarly will display an image of the ancillary tool on the display device 34 that changes in size depending on the distance D to the ancillary tool, which is positioned on or adjacent to the subject 50. Consequently, an approach similar to the above-described features for regarding measuring IPD can be employed. The characteristic feature size of the ancillary tool is known either in pixels for that desired distance or via a conversion to the actual feature size can be made for comparison. The advantage of this approach is in the ability to define features of the ancillary tool which can facilitate the image processing necessary to locate it in the image and characterize it in terms of pixels.

The application 52 may be further configured to determine a rotational angle $\theta_R$ of the head or the face 55 of the subject 50 (e.g., tilt angle). Using the eye pupil pixel coordinates of the left eye pupil 56L and the right pupil 56L in the image 54, the application 52 may calculate a rotational angle $\theta_R$ of the face 55 relative to the camera by calculating the angle of the centerline L between the left eye pupil 56L and the right pupil 56L compared to the horizontal axis of the camera sensor. The rotational angle $\theta_R$ is defined as rotation about an imaginary axis extending in a direction parallel to an optical axis of the subject's eyes, or an imaginary axis extending along the optical axis of the image-capturing device 44. The application 52 may include a predetermined head maximum rotation threshold $\theta_T$ stored on the data storage unit 48. The application 52 may compare the calculated rotational angle $\theta_R$ and the rotation threshold $\theta_T$, and perform a remediation action if the application 52 determines that the calculated rotational angle $\theta_R$ equals or exceeds the rotation threshold $\theta_T$. The remediation action may include providing a visual indication on the display device 34, such as displaying the text "subject is not facing the camera", or disabling the image capture tool 53 to prevent capturing and storing an image until the calculated rotational angle $\theta_R$ does not equal or exceed the rotation threshold $\theta_T$. The rotation threshold $\theta_T$ provides a metric to define the maximum head tilt tolerated for photorefraction. Typically, rotational position should be less than 15° (i.e., rotation threshold $\theta_T$=15°); however, rotation threshold $\theta_T$ levels other than 15° are considered to be within the scope of the current disclosure.

The application 52 may also calculate gaze angle using a method of location of cornea reflex eccentricity compared to eye pupil or limbus center (Hirschberg Ratio, or modifications thereof). Gaze angle is defined as the angle between the light-generating device 38 and the optical axis of the subject's 50 eyes. Gaze angle should be less than 15 degrees for adequate photorefraction estimation.

Light level is an important metric to monitor to ensure proper photorefraction measurements. The application 52 may include an illumination evaluation component that can, using the image-capturing device 44, measure the scene light or illuminance in the image 54, measured in lux. There is an acceptable range of illuminance for capturing and storing an image of the subject's eye pupils 56L and 56R for performing the photorefractive assessment. For image-capturing devices 44 without infrared ranging, the illuminance should be bright enough to center the image-capturing device 44 on the subject 50, but dark enough to allow the eye pupils 56L and 56R to be sufficiently large to properly conduct the photorefractive assessment. In particular, minimum eye pupil diameter should be greater than 3 mm, and optimally no smaller than 4 mm for good photorefraction estimation.

Figure 10A:
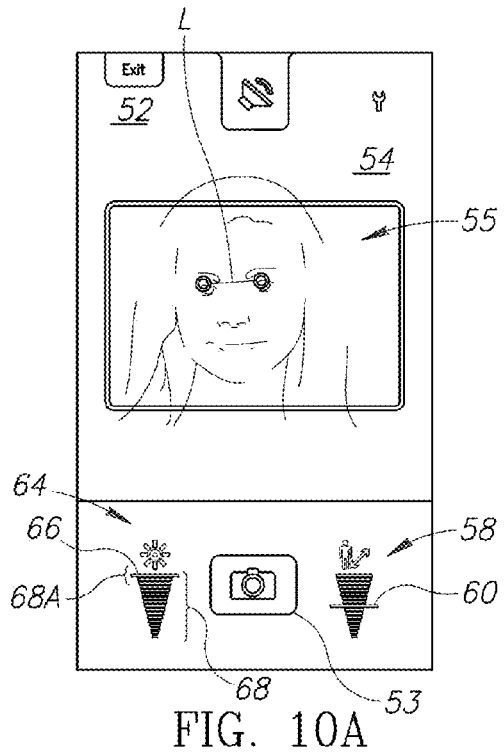
FIG. 10A illustrates a fourth screen of the application of FIG. 9A.
Figure 10B:
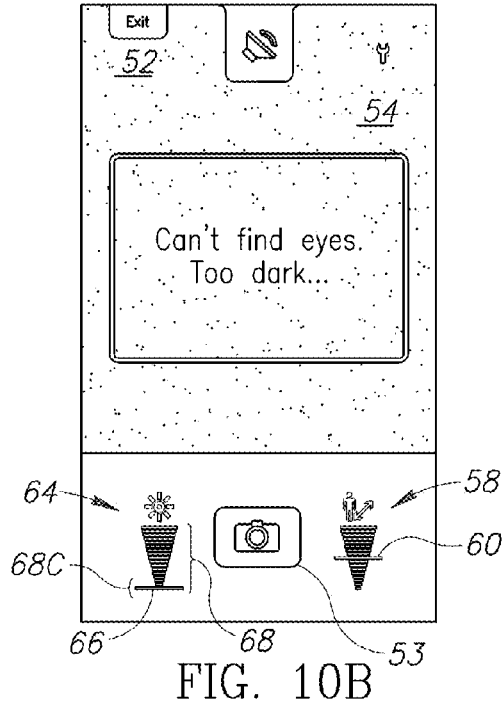
FIG. 10B illustrates a fifth screen of the application of FIG. 9A.
Figure 10C:
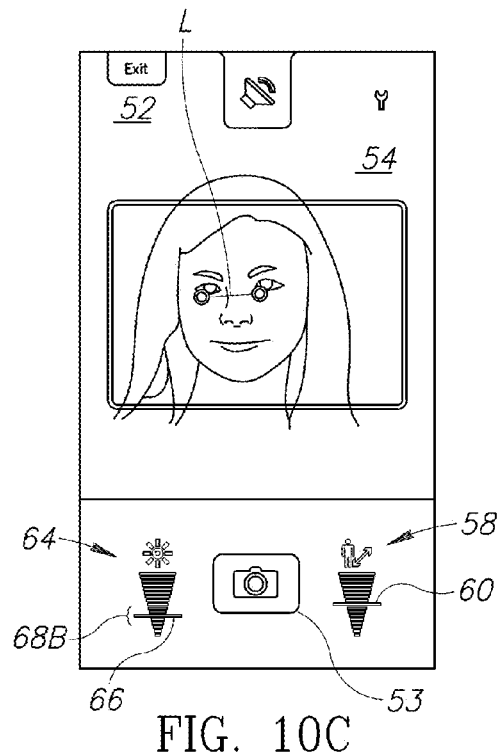
FIG. 10C illustrates a sixth screen of the application of FIG. 9A.

The illumination evaluation component of the application 52 may determine a current light level feedback based on information provided in the image 54. The application 52 may include an illuminance indicator 64 displayed on the display device 34 that indicates whether the illuminance level $E_V$ of the image 54 is appropriate for performing a photorefractive assessment, as shown in FIGS. 10A through 10C. The application 52 may provide the user with adequate feedback to allow eye pupil dilation necessary for accurate photorefraction measurement. The illuminance indicator 64 may include a level indicator 66 indicating a current illuminance level $E_V$ in the image 54 displayed relative to an illuminance range 68. The illuminance range 68 may be divided into different ranges 68A-68C having different colors. The application 52 may compare the current illuminance level $E_V$ with an acceptable illuminance range ($E_{min}$ to $E_{max}$), typically defined as between 5 lux and 20 lux, inclusive. Alternatively, the illuminance indicator 64 may include a numerical indication 67 of the luminance level $E_V$ (see FIG. 9C).

If the illuminance level is not within the acceptable illuminance range, then the application 52 may perform a remediation action to help ensure that the image captured satisfactory are optimal for performing photorefractive analysis. The application 52 will display the level indicator 66 relative to the illuminance range 68 based on the illuminance level $E_V$ determined. If the illuminance level $E_V$ is too bright (i.e., $E_V > E_{max}$), the illuminance level 66 will be positioned within a first range 68A, as shown in FIG. 10A. If the illuminance level $E_V$ is too dark (i.e., $E_V < E_{min}$), the illuminance level 66 will be positioned within a third range 68C, as shown in FIG. 10B. The remediation action performed by the application 52 may include displaying a message on the display device 34, such as "too dark" or "too bright", displaying a washed out or dark image on the display device 34, or disabling the image-capturing tool 53 such that a user is unable to capture an image using the image-capturing device 44 unless the illuminance level $E_V$ is acceptable. If the illuminance level $E_V$ is within the acceptable illuminance range 68B (i.e., $E_{min} < E_V < E_{max}$), the application 52 determines that the illuminance $E_V$ is appropriate for performing a photorefractive assessment and does not perform a remediation action, as shown in FIG. 10C.

Once conditions are appropriate for capturing an image for performing a photorefractive assessment (i.e., the subject 50 is correctly oriented, the subject 50 is positioned at an appropriate distance D, and the illuminance level $E_V$ is appropriate), the high resolution image is captured and stored on the data storage unit 34. The application 52 may have an analysis component configured to analyze the captured image and provide feedback on the display device 34 about the quality of the captured image. The analysis component may use image features evaluated to determine the quality of the acquired photo prior to acceptance as a valid photorefraction measurement. These features may include but are not limited to eyelids, eye pupil position, limbus position, images of reflected room features, eye pupil size, and the relationship between the positions of these features. In addition, the cornea reflex ($1^{st}$ Purkinje reflection) may be used alone or in conjunction with other measured features to determine quality of the acquired photo. For example, the relationship between the cornea reflex and the center of the eye pupil (or the center of the limbus) may be used to calculate the gaze angle error.

Figure 11:
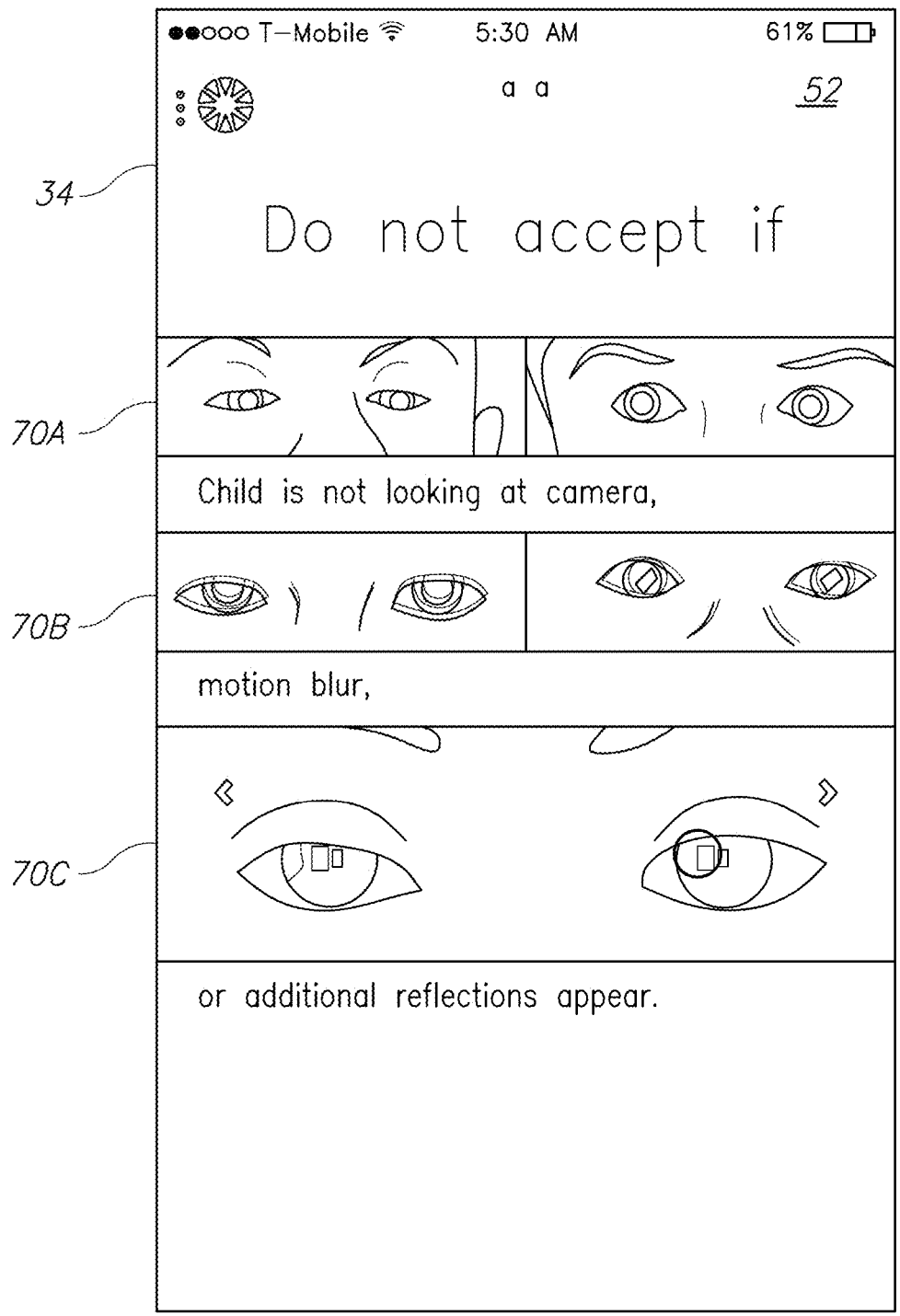
FIG. 11 illustrates a seventh screen of the application of FIG. 9A.

If the application 52 determines that the quality of the captured image is insufficient or that there is a defect in the captured image based on the analysis, the application 52 may display a message on the display device 34 identifying a deficiency. For example, the subject 50 may move abruptly, causing motion blur in the captured image 70B (especially for infants and younger children), as shown in FIG. 11. Ideally, motion blur should be less than a pixel, but no more than 3 pixels. If blur is detected in the captured image, the application 52 may reject the captured image or display a message alerting the user of motion blur in the captured image 70B.

Another condition to monitor is the gaze angle of the eye, where the head of the subject 50 head may be directed towards the camera, but the eyes are looking sideways, as shown in the captured image 70A of FIG. 11. The analysis component of the application 52 may be configured to determine whether the gaze angle of the eyes in the captured image is acceptable. If the application 52 detects an unacceptable gaze angle in the captured image, as shown in FIG. 11, the application 52 may reject the captured image 70B or display a message alerting the user of the unacceptable gaze angle in the captured image 70B. The analysis component may be configured to detect additional reflections that may make performing the photorefractive assessment on the captured image difficult or impossible, as shown in the captured image 70C of FIG. 11. If the application 52 detects additional reflections in the captured image, as shown in FIG. 11, the application 52 may reject the captured image 70C or display a message alerting the user of the additional reflections in the captured image 70C. These are just a few examples of how image processing can be used to ensure the operator takes high-fidelity images prior to further processing. Other conditions include (but are not limited to) camera defocus, or strabismus.

Once an appropriate image has been captured using the image-capturing device 44 and stored on the data storage unit 48, the application 52 performs a photorefractive assessment of the image and displays results to the user. For example, the results of the photorefractive assessment may measure refraction of a subject's eyes.

The application 52 may be configured to utilize the above-described method using the image-capturing device 36 and the light-generating device 38 on the front side 32 of the computing device 30 instead of the ones on the back side 40. In such a configuration, the application 52 allows a subject to administer the above-described method without assistance from another person.

An optical device may be attached to the computing device 12 without deviating from the method and system disclosed herein. A prism or other optical device, for instance, may be positioned over the light-generating device 38 or 42 to change the effective position, diffusion, refraction, etc. of the light generated by the computing device 12.

A lens (e.g., Gaussian telescope) may be positioned over the image-capturing device 36 or 44 to increase the resolution or change its effective position on the computing device 12. The optical device may be a part of a cover for the computing device 12 or a standalone device.

The application 52 may be part of an integrated suite of mobile vision diagnostics available in an application, which includes other diagnostic tests and may include a variety of educational features, as described in U.S. Non-Provisional application Ser. No. 15/333,039, filed Oct. 24, 2016, entitled "VISUAL ACUITY TESTING METHOD AND PRODUCT," which is incorporated by reference in its entirety.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

What is claimed is:

1. A computer-implemented method of performing a specified ophthalmologic assessment, the method comprising:
receiving an input specifying subject information on a handheld computing device;
capturing an image, using an image-capturing device of the handheld computing device, containing a left eye pupil and a right eye pupil of a subject;
analyzing the image captured on a processing unit of the handheld computing device to determine a position of the left eye pupil of the subject and a position of the right eye pupil of the subject in the image captured;
measuring, using the processing unit, an interpupilary distance between the position of the left eye pupil and the position of the right eye pupil;
determining, using the processing unit, a distance from the image-capturing device to a subject's eyes based on a comparison of the interpupilary distance measured with a predetermined interpupilary distance corresponding to the subject information;
determining whether the distance determined is within an appropriate distance range for performing the specified ophthalmologic assessment; and
in response to a determination that the distance determined is not within the appropriate distance range, causing the handheld computing device to perform a remediation action.

2. The computer-implemented method of claim 1, wherein the specified ophthalmologic assessment is a photorefractive assessment.

3. The computer-implemented method of claim 1, wherein the subject information specifies an age and a sex of the subject, and the predetermined interpupilary distance corresponds to the age and sex specified in the subject information.

4. The computer-implemented method of claim 1, wherein the remediation action is providing an indication on a display of the handheld computing device that the distance is not within the appropriate distance range.

5. The computer-implemented method of claim 1, further comprising:
analyzing the image captured to determine an illuminance level of the image captured;
determining whether the illuminance level is within an appropriate illuminance range for performing the specified ophthalmologic assessment; and
in response to a determination that the illuminance level is not within the appropriate illuminance range, causing the handheld computing device to perform a second remediation action.

6. The computer-implemented method of claim 5, wherein the second remediation action is providing an indication on a display of the handheld computing device that the illuminance level is not within the appropriate illuminance range.

7. The computer-implemented method of claim 1, wherein the method further comprises:
analyzing the image captured to determine a rotational angle of a head of the subject based on an angle of a centerline of the subject's pupils relative to a horizontal axis of the image-capturing device, the centerline of the subject's pupils extending between the position of the left eye pupil and the position of the right eye pupil;
determining whether the rotational angle of the head is within an appropriate rotational angle range for performing the specified ophthalmologic assessment; and
in response to a determination that the rotational angle of the head is not within the appropriate rotational angle range, causing the handheld computing device to perform a second remediation action.

8. A handheld computing system for providing a specified ophthalmologic assessment for a subject's eyes, the handheld computing system comprising:
an image-capturing device;
a display;
a data storage unit comprising an application including programming data;
a processing unit operatively coupled to the image-capturing device, the display, and the data storage unit, execution of the programming data causing the processing unit to:
receive an input specifying subject information on the handheld computing device;
capture an image, using the image-capturing device, containing a left eye pupil and a right eye pupil of the subject;
analyze the image captured on the processing unit to determine a position of a left eye pupil of the subject and a position of a right eye pupil of the subject in the image captured;
measure an interpupilary distance between the position of the left eye pupil and the position of the right eye pupil;
determine a distance from the image-capturing device to the subject's eyes based on a comparison of the interpupilary distance measured with a predetermined interpupilary distance corresponding to the subject information;
determine whether the distance determined is within an appropriate distance range for performing the specified ophthalmologic assessment; and
in response to a determination that the distance determined is not within the appropriate distance range, perform a remediation action.

9. The handheld computing system of claim 8, wherein the specified ophthalmologic assessment is a photorefractive assessment.

10. The handheld computing system of claim 8, wherein the subject information specifies an age and a sex of the subject, and the predetermined interpupilary distance corresponds to the age and sex specified in the subject information.

11. The handheld computing system of claim 8, wherein the remediation action is providing an indication on the display that the distance is not within the appropriate distance range.

12. The handheld computing system of claim 8, execution of the programming data further causing the processing unit to:
analyze the image captured to determine an illuminance level of the image captured;
determine whether the illuminance level is within an appropriate illuminance range for performing the specified ophthalmologic assessment; and
in response to a determination that the illuminance level is not within the appropriate illuminance range, perform a second remediation action.

13. The handheld computing system of claim 12, wherein the second remediation action is providing an indication on the display that the illuminance level is not within the appropriate illuminance range.

14. The handheld computing system of claim 8, execution of the programming data further causing the processing unit to:

analyze the image captured to determine a rotational angle of a head of the subject based on an angle of a centerline of the subject's pupils relative to a horizontal axis of the image-capturing device, the centerline of the subject's pupils extending between the position of the left eye pupil and the position of the right eye pupil;

determine whether the rotational angle of the head is within an appropriate rotational angle range for performing the specified ophthalmologic assessment; and in response to a determination that the rotational angle of the head is not within the appropriate rotational angle range, perform a second remediation action.

15. A non-transitory computer readable medium having computer-executable components that, when executed by a handheld computing device having an image-capturing device, a display, and a processing unit, cause the handheld computing device to:

receive an input specifying subject information on the handheld computing device;

capture an image, using the image-capturing device, containing a left eye pupil and a right eye pupil of a subject;

analyze the image captured on the processing unit to determine a position of a left eye pupil of the subject and a position of a right eye pupil of the subject in the image captured;

measure an interpupilary distance between the position of the left eye pupil and the position of the right eye pupil;

determine a distance from the image-capturing device to the subject's eyes based on a comparison of the interpupilary distance measured with a predetermined interpupilary distance corresponding to the subject information;

determine whether the distance determined is within an appropriate distance range for performing a specified ophthalmologic assessment; and in response to a determination that the distance determined is not within the appropriate distance range, perform a remediation action.

16. The non-transitory computer readable medium of claim 15, wherein the specified ophthalmologic assessment is a photorefractive assessment.

17. The non-transitory computer readable medium of claim 15, wherein the subject information specifies an age and a sex of the subject, and the predetermined interpupilary distance corresponds to the age and sex specified in the subject information.

18. The non-transitory computer readable medium of claim 15, wherein the remediation action is providing an indication on the display that the distance is not within the appropriate distance range.

19. The non-transitory computer readable medium of claim 15, wherein execution of the computer-executable components further causes the handheld computing device to:

analyze the image captured to determine an illuminance level of the image captured;

determine whether the illuminance level is within an appropriate illuminance range for performing the specified ophthalmologic assessment; and in response to a determination that the illuminance level is not within the appropriate illuminance range, perform a second remediation action.

20. The non-transitory computer readable medium of claim 19, wherein the second remediation action is providing an indication on the display that the illuminance level is not within the appropriate illuminance range.

21. The non-transitory computer readable medium of claim 15, wherein execution of the computer-executable components further causes the handheld computing device to:

analyze the image captured to determine a rotational angle of a head of the subject based on an angle of a centerline of the eye pupils of the subject relative to a horizontal axis of the image-capturing device, the centerline of the eye pupils of the subject extending between the position of the left eye pupil and the position of the right eye pupil;

determine whether the rotational angle of the head is within an appropriate rotational angle range for performing the specified ophthalmologic assessment; and in response to a determination that the rotational angle of the head is not within the appropriate rotational angle range, perform a second remediation action.

* * * * *